United States Patent [19]

Calabrese

[11] 4,335,718
[45] Jun. 22, 1982

[54] NEEDLE CANNULA

[75] Inventor: Frank B. Calabrese, West Caldwell, N.J.

[73] Assignee: Becton, Dickinson and Company, Paramus, N.J.

[21] Appl. No.: 193,055

[22] Filed: Oct. 2, 1980

[51] Int. Cl.³ .............................................. A61M 5/00
[52] U.S. Cl. ................................. 128/218 N; 128/221
[58] Field of Search ................... 128/218 N, 221, 347, 128/214.4, 213

[56] References Cited

U.S. PATENT DOCUMENTS 3,388,703 6/1968 Bowes ............................. 128/221 X
4,020,837 5/1977 Larson ............................. 128/218 N
4,250,881 2/1981 Smith ............................... 128/221 X

FOREIGN PATENT DOCUMENTS 1560782 3/1969 France ................................. 128/221
740221 11/1955 United Kingdom ........... 128/218 N Primary Examiner—John D. Yasko
Attorney, Agent, or Firm—Richard J. Rodrick

[57] ABSTRACT

A needle cannula comprises a hollow tubular member having a first portion and a second portion terminating in a sharp point. The outside diameter of the second portion is less than the outside diameter of the first portion, while the inside diameter of the second portion is not less than the inside diameter of the first portion.

8 Claims, 7 Drawing Figures

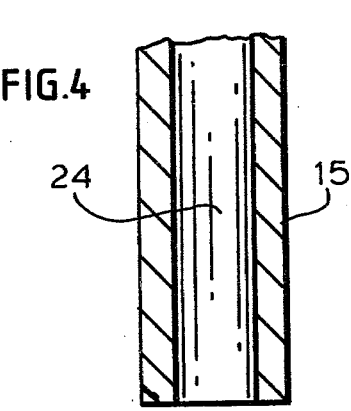
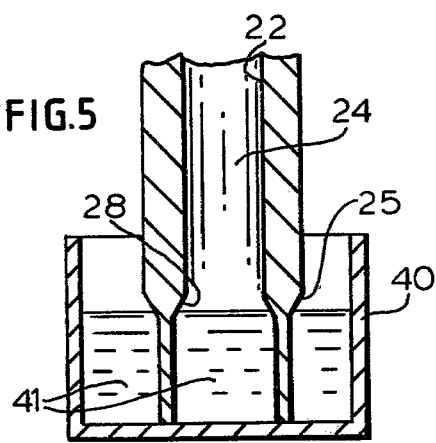
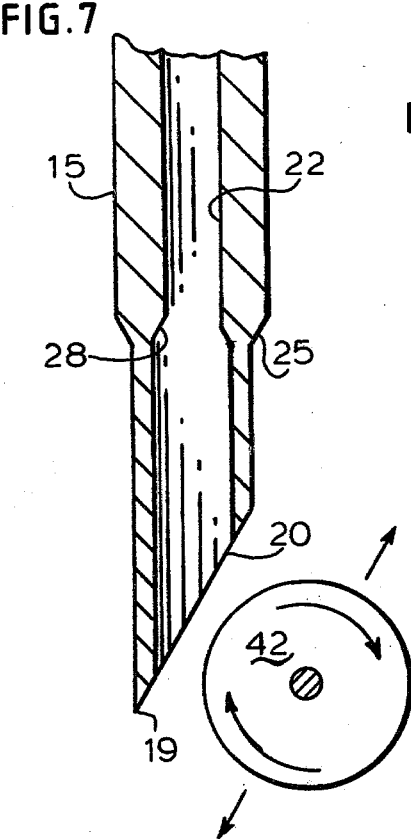
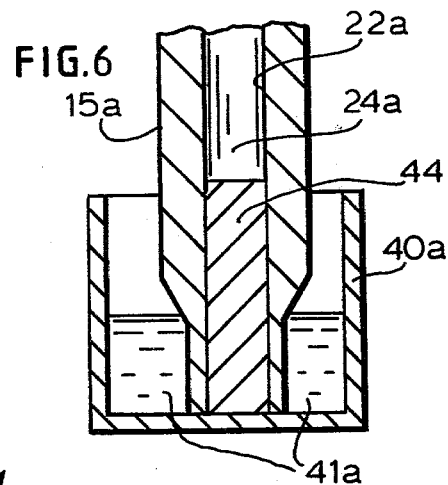

NEEDLE CANNULA

BACKGROUND OF THE INVENTION

1. Field of the Invention

The present invention relates to a hollow, fluid conveying needle, and more particularly, concerns a needle cannula with an improved pointed end which is intended primarily for penetration of the skin of a patient.

2. Description of the Prior Art

When using a hollow needle cannula for the conveyance of fluid particularly through the skin of a patient, a number of significant factors must be considered in the design of such cannula. For instance, the needle cannula should be sufficiently rigid and stiff so that it can effectively penetrate the skin of the patient without breaking or bending to such a degree so as to occlude the fluid path. In this regard, such needle cannulae are primarily made of metal so as to impart these desired stiffness characteristics. In addition to surface lubricity of the needle and the sharpness of the point, the outside diameter of the needle and its wall thickness play a factor in the penetration of the skin and the discomfiture attendant with such penetration. It has been suggested that reduction in the outside diameter and the wall thickness of the needle will provide greater ease in penetration of the skin of the patient. However, there is usually a tradeoff in merely reducing the outside diameter of the needle in order to achieve this desired ease of penetration. This tradeoff generally involves a narrowing or constriction of the inside diameter of the needle along with the reduction of the outside diameter of the needle. As a result, the flow rate capability through the needle is impaired, especially if large flow rates or quantities of fluid are to be conveyed through the needle. Furthermore, merely reducing the wall thickness of the needle will compromise the stiffness characteristics of the needle so that there will be a greater tendency to bend or break during its use.

In U.S. Pat. No. 3,540,447, a spinal needle is disclosed in which the pointed end has a reduced diameter when compared to the remainder of the needle. It can be seen, however, that the inside lumen of this patented needle has a smaller cross-sectional dimension than the lumen in the enlarged portion of the needle. As a result, any fluid flowing through this patented needle will be subject to flow rate deviations through the narrow pointed end of the needle. Another patent which discloses a reduced diameter point on the needle is U.S. Pat. No. 3,216,616.

With the foregoing in mind, improvements are still being sought in the point end of a needle cannula which will overcome many of the deficiencies noted above.

SUMMARY OF THE INVENTION

A needle cannula of the present invention comprises a hollow tubular member having a first portion and a second portion terminating in a sharp point. The second portion has its major outside dimension less than the major outside dimension of the first portion, while its wall thickness is less than the wall thickness of the first portion.

In a preferred embodiment of this aspect of the invention, the hollow tubular member is a substantially cylindrical metal barrel in which its distal portion terminates in an angled sharp point for the penetration of skin. This distal portion has its outside diameter less than the outside diameter of the proximal portion preferably including a tapered transition surface between respective outside diameters. This distal portion also has an inside diameter greater than the inside diameter of the proximal portion, again with a preferred tapered transition surface between respective inside diameters.

Another aspect of the present invention includes a method of making a needle cannula from a finite length of hollow, substantially cylindrical tubing having a proximal portion and a distal portion. This method includes reducing the outside diameter at the distal portion so that it is less than the outside diameter at the proximal portion. The method further includes controlling the inside diameter at the distal portion so that it is not reduced to a diameter less than the inside diameter at the proximal portion. A sharp point is formed at the terminal end of the distal portion.

In a preferred embodiment of the method aspect of the present invention, the reducing step is performed by etching the distal end of the needle. Electro-chemical or chemical etching is the preferred process for performing this step of the method.

In accordance with the principles of the present invention, the needle cannula herein retains many of the characteristics of standard needles inasmuch as the reduced diameter distal portion is only at the very end of the needle, thereby allowing the needle to retain its stiffness and rigidity characteristics. On the other hand, the reduced diameter distal portion does not constrict the inside diameter of the distal portion so that it is less than the inside diameter of the remainder of the needle. In this fashion, the flow rate through the needle of the present invention is not restricted and can handle the same flow rate as needles without reduced outside diameters. Moreover, the present invention contemplates a needle cannula in which both the outside diameter of the distal portion and its wall thickness are reduced to contribute to ease of penetration through the skin of the patient. Fabrication of the needle cannula of the present invention lends itself to a number of convenient processes of manufacture, with electro-chemical or chemical etching being most preferred.

BRIEF DESCRIPTION OF THE DRAWINGS

FIG. 4 is a cross-sectional view of hollow tubular material as it would appear before the improved pointed end is formed thereon;

FIG. 5 is a sectional view illustrating the tubular needle material of FIG. 4 being placed in an etching bath in order to modify the distal end of the tubular needle material;

FIG. 6 is a process similar to FIG. 5 illustrating in cross-section an alternative method of forming the distal end of the needle cannula in accordance with the embodiment of FIG. 3; and FIG. 7 illustrates one embodiment, in cross-section, of forming the sharp point at the distal end of the needle cannula.

DETAILED DESCRIPTION

Figure 1:
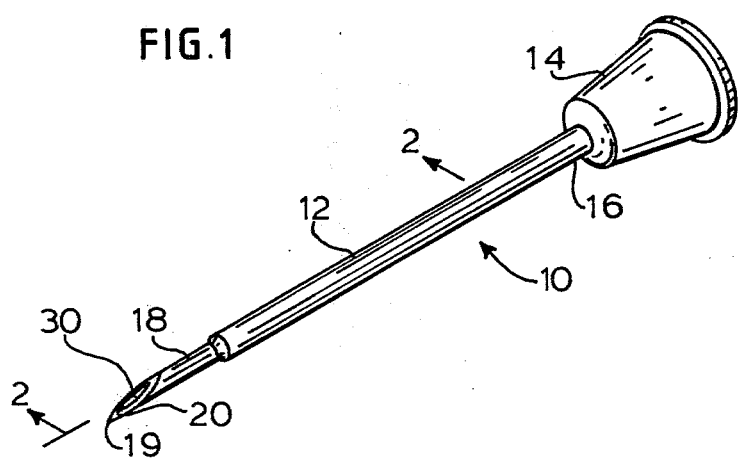
FIG. 1 is a perspective view illustrating the preferred embodiment of the needle cannula of the present invention as it may appear connected to a needle hub.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Adverting now to the drawings, and FIG. 1 in particular, there is illustrated a needle assembly 10 which is useful in medical applications for the conveyance of fluid therethrough. Assembly 10 includes a needle cannula 12 which is connected to a hub 14 which serves as a connecting medium through which fluid is either delivered or extracted through the assembly. It is appreciated that needle cannula 12 may be used in other applications in which the hub element may vary in configuration or may be eliminated altogether if other connections to the needle cannula are feasible.

Figure 2:
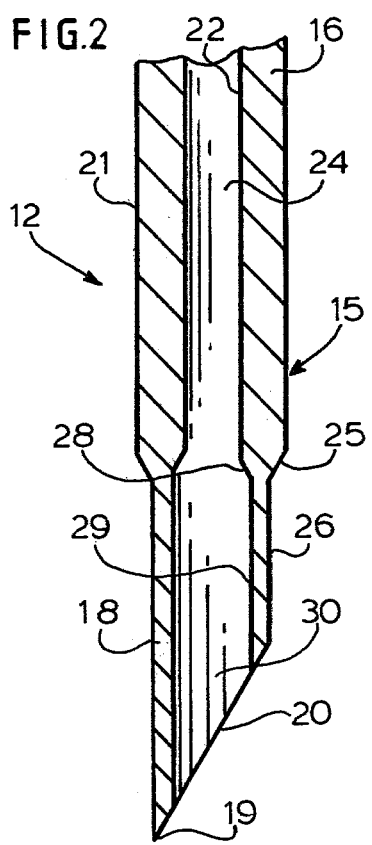
FIG. 2 is an enlarged cross-sectional view taken along line 2—2 of FIG. 1.

Turning now to FIG. 2, taken in conjunction with FIG. 1, needle cannula 12 is illustrated in greater detail. This needle cannula is preferably formed from an elongate, hollow, substantially cylindrical tubular barrel 15. Barrel 15 has a proximal end 16 which will be the end of the cannula facing toward hub 14 in the embodiment illustrated in FIG. 1, or otherwise facing away from the pointed end of the needle cannula. Distal end 18 is at the other end of barrel 15 and is the portion of the needle which includes a sharp point 19 intended for penetration of the skin of the patient. In order to allow greater ease of penetration through the skin, point 19 is formed at the end of an angled surface 20 at the distal end of the needle cannula.

Proximal portion 16 of the cannula includes an outside diameter 21 and an inside diameter 22 thereby forming a hollow passageway 24 therein. In the transition region between proximal and distal portions of the cannula, a tapered transition surface 25 tapers inwardly from the proximal portion toward the distal portion of the cannula. As a result of this transition, the outside diameter 26 of the distal portion is less than outside diameter 21 on the proximal portion. Similarly, in the embodiment being described, in the transition region between proximal and distal portions, there is a tapered transition surface 28 on the inside diameter of the cannula extending from the proximal portion toward the distal portion. As a result of tapered surface 28, inside diameter 29 of the distal portion is greater than inside diameter 22 of the proximal portion. The effect of tapered surfaces 25 and 28 thereby provides a reduction in the wall thickness of the distal portion compared to the wall thickness of the proximal portion of this needle cannula. This, in turn, provides an enlarged passageway 30 through the distal portion. The reduced outside diameter and wall thickness of the distal portion thereby provides a contribution to making penetration of the skin of the patient easier. Stiffness of the needle cannula is not significantly compromised, if at all, inasmuch as the reduced outside diameter and wall thickness of the distal end occurs at the very end of the cannula itself. Typically, this small reduced portion of the needle cannula may be in the order of one-quarter inch (0.63 centimeters) if the total length of the needle cannula is 1.0 inches (2.54 centimeters).

Figure 3:
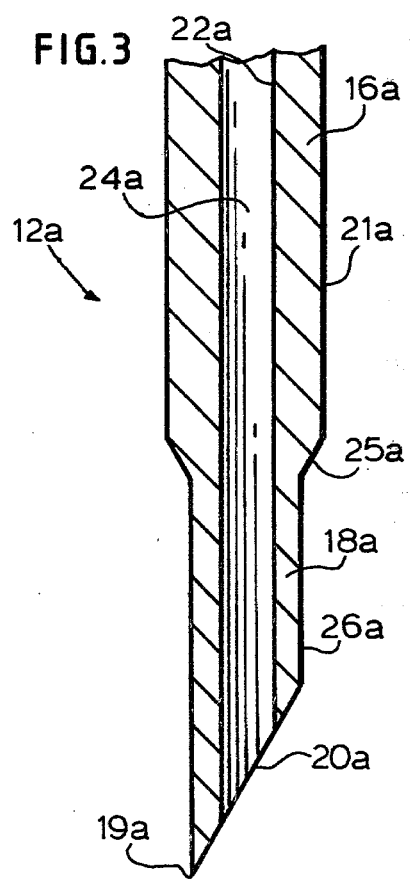
FIG. 3 is an enlarged cross-sectional view of an alternate embodiment of the needle cannula illustrated in FIG. 2.

Turning now to FIG. 3, an embodiment alternate to that of FIG. 2, but similar in many respects, is illustrated. In fact, the only difference between the embodiment of FIG. 3 and that of FIG. 2 is the elimination of the tapered surface on the inside diameter of the cannula. As a result, inside diameter 22a is the same for both proximal portion 16a and for distal portion 18a. However, inasmuch as tapered transition surface 25a remains on the outside diameter of the cannula, outside diameter 26a of the distal portion is less than outside diameter 21a of the proximal portion. Also, the wall thickness of the distal portion is less than the wall thickness of the proximal portion. In the embodiments illustrated in both FIGS. 2 and 3, the reduced outside diameter of the distal portion and its wall thickness are factors which contribute to the ease of penetration through the skin.

In FIGS. 4, 5 and 7, a preferred method is illustrated for fabricating needle cannula 12 as illustrated in FIGS. 1 and 2. Particularly referring to FIG. 4, barrel 15 is illustrated as being a finite length of hollow, substantially cylindrical tubing, preferably made out of metal for the ensuing etching process. Metal such as medical grade stainless steel is primarily adapted for use as needle cannula in medical applications, and provides the desired stiffness and rigidity characteristics to assure the ability to satisfactorily penetrate the skin of the patient.

In FIG. 5, the barrel 15 is placed in a receptacle 40 containing a liquid etching material 41. Barrel 15 is placed a controlled distance into etching material 41 while its passageway 24 remains open. As a result of this placement, the etching material contacts both the interior and exterior surfaces of the barrel. The chemical etching material will then work on the wall thickness of the barrel so that the outside diameter of the barrel placed in the bath will be reduced, whereas the inside diameter of the barrel in the bath will be expanded as compared to respective outside and inside diameters of the barrel outside of the etching material. Tapered surfaces 25 and 28 will be formed in this etching process by virtue of the etching material creeping upwardly a sufficient amount to result in tapered surfaces in the transition region between the portion of the barrel contacted by the etching material and that portion not in contact with the etching material. When the desired wall thickness of the distal end of the barrel is achieved, the barrel is removed from the etching material and cleaned and rinsed. Sharp point 19 and angled surface 20 are then formed at the distal end of the barrel preferably by grinding such as with a grinding wheel 42. Grinding wheel 42 is appropriately powered (not shown) to turn at sufficient speed to bevel surface 20 on the desired angle and leave a sharp leading edge 19 at the distal end of the barrel. Grinding wheel 42 and/or needle cannula 15 are adapted to move in various directions, back and forth or in and out, in order to provide the desired shape to angled surface 20. It is appreciated that other operations for placing a sharp point at the distal end of the needle cannula are contemplated by and fall within the purview of the present invention.

Turning now to FIG. 6, the method of FIG. 5 is slightly modified in order to fabricate the needle cannula as illustrated in FIG. 3. Instead of leaving passageway 24a open, a snug fitting mandrel 44 is placed in tight contact with inside diameter 22a of barrel 15a. It is the purpose of mandrel 44 to mask off the interior of barrel 15a during the etching process. As a result, when the distal end of the barrel is formed, etching material

41a is prevented from contacting the inside diameter of the barrel. Accordingly, the wall thickness of the distal end of the barrel is reduced by having only the outside diameter of the distal portion reduced by virtue of the chemical etch. It is understood that masking elements other than a snug fitting mandrel may be used in order to prevent the etching material from contacting the inside diameter of the tubular barrel.

Moreover, instead of chemical etching, the above-described processes may be modified by employing an electro-chemical etching procedure. In using an electro-chemical etching procedure, various electrodes are employed to deliver current to the electrically conductive barrel in conjunction with a chemically corrosive material to produce a chemical change in the material so subjected. The effect of this process will be to corrode the surfaces of the material to which the process is applied thereby reducing the thickness of the remaining unattacked material.

Thus, the present invention provides a needle cannula particularly useful for the conveyance of liquid therethrough which not only facilitates the penetration of the skin of the patient, but also maintains its rigidity and stiffness for insertion purposes and does not reduce the effectiveness of the fluid flow rates which the needle cannula is designed to accommodate.

What is claimed is:

1. A needle cannula for the conveyance of liquid therethrough comprising: an elongate, hollow, substantially cylindrical barrel having a proximal portion and a distal portion terminating in a sharp point for the penetration of skin, said distal portion having an outside diameter less than the outside diameter of said proximal portion, the inside diameter of said distal portion being greater than the inside diameter of said proximal portion.

2. The needle cannula of claim 1 wherein the transition surface between the outside diameters of proximal and distal portions is tapered.

3. The needle cannula of claim 1 wherein the transition surface between the inside diameters of proximal and distal portions is tapered.

4. The needle cannula of claim 1 wherein said point is angled to form a leading sharp edge.

5. The needle cannula of claim 1 wherein said barrel is made of metal.

6. The needle cannula of claim 5 wherein said metal is medical grade stainless steel.

7. The needle cannula of claim 1 wherein the distal portion is a minority portion of the entire needle cannula.

8. A needle cannula for the conveyance of a liquid therethrough comprising:
an elongate, hollow, substantially cylindrical metal barrel having a proximal portion and a distal portion terminating in an angled sharp point for the penetration of skin, said distal portion having an outside diameter less than the outside diameter of said proximal portion with a tapered transition surface between said respective outside diameters, said distal portion having an inside diameter greater than the inside diameter of said proximal portion with a tapered transition surface between said respective inside diameters.

* * * * *